United States Patent [19]

Wood et al.

[11] Patent Number: 4,971,793

[45] Date of Patent: Nov. 20, 1990

[54] SUBUNIT CANINE PARVOVIRUS VACCINE

[75] Inventors: Harry A. Wood, Ithaca, N.Y.; Colin R. Parrish, Victoria, Australia

[73] Assignees: Boyce Thompson Institute for Plant Research, Inc.; Cornell Research Foundation, Inc., both of Ithaca, N.Y.

[21] Appl. No.: 191,684

[22] Filed: May 9, 1988

[51] Int. Cl.[5] .......................................... A61K 39/175

[52] U.S. Cl. ......................................... 424/88; 424/89

[58] Field of Search ...................... 424/88, 89; 935/65; 435/235, 5

[56] References Cited

U.S. PATENT DOCUMENTS 4,193,990  3/1980  Appel et al. .......................... 424/89
4,193,991  3/1980  Appel et al. .......................... 424/89
4,303,645  12/1981 Carmichael et al. .................. 424/89

OTHER PUBLICATIONS

Parrish et al., Antigenic Relationships Between Canine Parvovirus Type-2, Feline Panleukopenia Virus . . . 1982 Archives of Virology 72, pp. 267-278.
Parrish et al., Antigenic Structure and Variation of Canine Parvovirus Type -2, Feline Panleukopenia Virus, . . . 1983 Virology 129, pp. 401-414.
Luckow et al., Trends in the Development of Baculovirus Expression Vectors 1988 Bio/Technology 6, pp. 47-55.
G. Smith et al., Molecular & Cellular Biology v3 (12) pp. 2156-2165, Dec. 1983
S. Halling et al., Chemical Abstracts v101 (25) 224015a, Dec. 17, 1984.
G. P. Mazzara et al., In "Vaccines, 87: Modern Approaches to New Vaccines: Prevention of AIDS & Other Viral, Bacterial & Parasitic Diseases", pp. 419-424, 9-1987/1986 Meeting.

Primary Examiner—Lester L. Lee
Assistant Examiner—Nina Ossanna
Attorney, Agent, or Firm—Ralph R. Barnard

[57] ABSTRACT

A recombinant subunit vaccine for protecting dogs against infection caused by canine parvovirus comprising VP-2 protein produced during replication of a recombinant baculovirus in insect tissue culture cells or insects which are a permissive host for the replication of selected baculoviruses.

6 Claims, No Drawings

SUBUNIT CANINE PARVOVIRUS VACCINE

BACKGROUND OF THE INVENTION

The general field of the invention is that of virus vaccines for protection of dogs against infection by canine parvovirus, their production and use. This invention is more particularly related to a subunit vaccine made by inserting canine parvovirus genes into a recombinant baculovirus expression vector. The vaccine is then produced by growing the resultant recombinant baculovirus in insect tissue culture or insects of a type which are a permissive host for the baculovirus replication and then harvesting the resulting vaccine material.

Parvovirus are characterized as small animal DNA viruses consisting of an isometric protein capsid and a short molecule of single-stranded DNA. Parvoviruses have been recovered and isolted from various animals over the years. Among them is the canine parvovirus which became an emerging disease of dogs in the world during a period beginning in 1978. At that time, the first canine parvovirus were isolated and vaccines were relatively rapidly developed to combat this disease which is characterized in dogs by diarrhea, fever, and leukopenia (relative lymphopenia). Starting in 1978, over the space of 3 years, 3 different kinds of canine parvovirus vaccines were developed to combat a wide spread outbreak of the then apparently new viral disease. They are reported as three landmark inventions by Professors in the Vaterinary Colleges of Cornell University, James A. Baker Institute for Animal Health. They are as follows:

(1) U.S. Pat. No. 4,193,991, issued Mar. 18, 1980 to Max J. G. Appel and Leland E. Carmichael which relates to an inactivated (killed) canine parvovirus vaccine.

(2) U.S. Pat. No. 4,193,990, issued on Mar. 18, 1980 to Max J. G., Appel, Leland E. Carmichael and Fredric W. Scott which relates to this use of the modified live or chemically activated feline panleukopenia virus as a canine parvovirus vaccine.

(3) U.S. Pat. No. 4,303,645, issued Dec. 1, 1981 to Leland E. Carmichael, Max J. G. Appel, and Douglas D. McGregor which relates to the use of the modified (attentuated) live canine parvovirus as a canine parvovirus vaccine.

These vaccines have functioned very well in the field over the years and have stemmed the outbreak of canine parvovirus all over the world. For the most part, this disease is well controlled following the proper vaccination program. However, the inactivated vaccines identified hereinabove tend to provide protection for a relatively short time and the modified live canine parvovirus vaccine is considered by some to have the potential for becoming virulent.

Over the years the canine parvovirus known as type-2 (CPV) has been studied by many and the DNA sequence of the same is reported in a scientific article entitled Parvovirus genome; Nucleotide sequence of H-1 and mapping of its genes by hybrid-arrested translation by Rhode et al. appearing in the Journal of Virology volume 54, pages 630–633. In addition Parrish et al. have studied the antigenic structure of canine parvovirus type-2 and have reported their work in a scientific article entitled Antigenic Structure and Variation of Canine Parvovirus Type-2 Feline Panleukopenia Virus, and Mink Enteritis Virus, in Virology volume 129 pages 401–414. This article identifies three protein categories relating to canine parvovirus antigenic reactivity, However, following the choice of many scientists for the purpose of describing the present invention, the description herein identifies only one of these categories which is viral protein VP-2 because it is the major immunogenic parvovirus capsid. Infection by canine parvovirus may be prevented by vaccinating animals with either live attenuated or inactivated virus vaccines. Antibody level is the prime mediator of protection. Several vaccines containing inactivated canine parvovirus have been marketed, but because of the small amounts of antigen present these generate low levels of short-lived immunity.

To produce more antigen than can be obtained from virus-infected cell cultures, several groups have attempted to develop vaccines by expressing portions of the CPV PV-2 gene in *E. coli* (see Carlson et al. 1984, Expression of feline panleukopenia virus antigens in *E. coli*. In Modern approaches to vaccines Cold Spring Harbor, N.Y. pages 195–201). Although these produce some VP-2 peptides, none has been shown to immunize animals efficiently or to express the intact antigenic sites of the protein responsible for neutralization. It appears that the VP-2 protein cannot be produced in *E. coli* expression systems in a form which will efficiently immunize animals and there is not a good vaccine to control canine parvovirus which is of significant veterinary importance.

A development relating to the use of baculovirus expression vectors to express foreign genes by recombinant baculoviruses offered a possibility to solve this important problem through further laboratory discovery. The prior art, with respect to baculovirus as it relates to the present invention is summarized in two scientific articles. They are:

1. "Production of Human Beta Interferon in Insect Cells Infected with a Baculovirus Express Vector", by Smith et al. appearing in Molecular and Cellular Biology, December 1983, volume 3, pages 2156 and 2165, and 2. "Trends in the Development of Baculovirus Expression Vectors", by Luckow et al. appearing in Bio/-Technology, January 1988, volume 6, pages 47–55.

The baculovirus vector has in other circumstances utilized the highly expressed and regulated *Autographa californica* nuclear polyhedrosis virus (AcMNPV) polyhedrin gene promoter and open reading frame modified for the insertion of foreign genes. Use of such a vector allows for the insertion of eukaryotic genes into the baculoviruses.

SUMMARY OF THE INVENTION AND DESCRIPTION OF PREFERRED EMBODIMENT

The *Autographa californica* nuclear polyhedrosis virus (AcMNPV) has several properties which make it well suited as a virus expression vector system. Most notably the AcMNPV contains a nonessential gene, the polyhedrin gene, which is under the control of the strong, late promoter (DNA sequences responsible for initiating mRNA transcription). Accordingly, this promoter directs the synthesis of large quantities of polyhedrin protein. In order to create a transfer plasmid which contains the AcMNPV polyhedrin promoter region, followed by a unique restriction enzyme site into which foreign genes could be inserted, a CPV gene coding for the production of VP-2 capsid protein was inserted into a baculovirus expression shuttle vector. It is identified herein as pAc 6C2B23, and is deposited in the American Type Culture Collection as number ATCC Designation 67 682 to be made available to the public in accordance to the rules and law related deposits for the purpose of filing patent application.

This transfer plasmid known as pAc 6C2B23 was used to insert the CPV VP-2 gene into *Autographa californica* nuclear polyhedrosis virus under the control of the said strong polyhedrin promoter of *Autographa californica* nuclear polyhedrosis virus, and that recombinant baculovirus (known as CPV C62B23) when inoculated into *Spodoptera frugiperda* tissue culture or the *Spodoptera frugiperda* larvae produced a high level expression of VP-2 protein as measured by indirect-florescent antibody labelling of infected and control tissue culture cells. In addition high levels of VP-2 protein were detected by pulse labelling with a radioactive aminoacid followed by acrylamide gel electrophoresis and autoradiography. Moreover, when the virus infected cells were injected subcutaneously into a canine to protect it against canine parvovirus the vaccinated animal was then challenged by a virulent reference canine parvovirus and the canine did not show any discernable sign of the disease. Whereas the canine that was used as a control and which was subject to the same conditions became seriously infected when it was challenged at the same time and in the same manner by the same virulent reference canine parvovirus.

A new recombinant subunit vaccine for canine parvovirus in canines was thereby discovered. The recombinant baculovirus CPV 6C2B23 faithfully produced in CPV VP-2 protein in insect cells that were immunogenic and protected the canine against challenge with a large dose of highly virulent canine parvovirus. The recombinant baculovirus is deposited in the American Type Culture Collection at 12301 Parklawn, Rockville, Md., 20857 under designation ATTC VR 2209.

It is accordingly an object of the present invention to provide a new and improved subunit canine parvovirus vaccine on using a baculovirus expression vector having a gene for producing VP-2 protein of canine parvovirus which was inserted into the corresponding baculovirus by transformation such that the CPV VP-2 gene was under the control of the strong polyhedrin promoter of *Autographa californica* virus and deriving that vaccine by inoculating Lepidopteran insect tissue culture cells or the Lepidopteran larvae themselves resulting in the production of VP-2 protein.

It is another object of the present invention to provide a new recombinant baculovirus identified as that on deposit at the American Type Culture Collection as designation ATCC VR 2209 as of Apr. 8, 1988.

It is still another object of the present invention to provide a new baculovirus expression vector of the type pAc 6C2B23 that is on deposit at the American Type Culture Collection as designation ATCC 67 682 as of Apr. 29, 1988.

While the present invention has been described as the use of a baculovirus expression vector for the expression of a canine parvovirus gene to produce VP-2 protein in abundance in the baculovirus *Autograph californica* nuclear virus (AcMNPV), the teachings of the present invention would apply equally to the other baculoviruses such as *Trichoplusia ni* MNPV, *Rachiplusia ou* MNPV or *Galleria mellonella* MNPV.

PREPARATION OF CPV, VP-2 GENE

Many scientist have isolated the VP-2 gene for canine parvovirus from a canine parvovirus type-2, which category is identified in a scientific publication entitled "Antigenic Relationships Between Canine Parvovirus Type-2 Feline Panleukopenia Virus and Mink Enteritis Virus Using Conventional Antisera and Monoclonal Antibodies", 1982 by Parrish et al., Archives of Virology, volume 72, pages 267-278. For the purpose of acquiring this gene, there are many canine parvovirus type-2 deposits, one of which is Cornell type strain 780916 (referred to as CPV-916). This strain (CPV-916) has been placed on deposit ascession No. VR-953 at the American Type Culture Collect, Rockville, Md. The CPV-916 strain may be obtained from ATCC or The James A. Baker Institute for Animal Health, New York State College of Veterinary Medicine at Cornell University, Ithaca, N.Y.

The canine parvovirus VP-2 gene open reading frame (DNA coding sequence) is contained within a 2.17 kbp fragment of DNA. BamHI linkers were attached to the ends of this fragment and inserted into the BamHI site of the transfer vector. The VP-2 gene contains approximately 50 bases upstream from the open reading frame of the gene.

BACULOVIRUS EXPRESSION VECTOR CONTAINING CPV GENES

The method of producing a recombinant baculovirus expression vector for *Autographa californica* nuclear polyhedrosis virus capable of expressing a CPV gene in Lepidopteran insect tissue culture cells or insects involves the following steps outlined in the article Luckow and Smith (1988) as referred to herein above on page 3:

1a. Cleaving the *Autographa californica* nuclear polyhedrosis virus DNA to isolate the EcoRI I fragment which contains the polyhedrin gene (promoter and open reading frame) and sufficient flanking DNA sequences to facilitate homologous recombination (FIG. 2, page 52).

1b. Deleting bases $-7$ to $+461$ ($+1$ is A of ATG) from the polyhedrin gene and inserting a BamHI linker.

1c. Preparing a recombinant expression vector for the *Autographa californica* nuclear polyhedorsis virus by inserting said DNA fragment into a cloning vehicle and thereafter inserting the genes for producing VP-2 protein of canine parvovirus type-2 into the thus modified cloning vehicle such that the said genes for producing VP-2 protein product of canine parvovirus is under the transcriptional control of the promoter for *Autographa californica* nuclear polyhedrosis virus.

Referring to FIG. 2 on page 52 of the article by Luckow and Smith (1988), the plasmid shown is nearly identical to the genetic construction of the present invention. The difference between base position $-7$ or $-8$ is inconsequential with regard to the effectiveness of the vaccine taught pursuant to the present invention. The enzymatic construction used to create the transfer plasmid of the present invention is the same as used to created plasmid pAc 373 as described in the Smith et al article appearing in Molecular and Cellular Biology, further identified on page 3, hereof.

INSERTING THE BACULOVIRUS VECTOR WITH A FOREIGN CPV GENES INTO THE BACULOVIRUS

Contacting said modified cloning vehicle DNA molecules with *Autographa californica* nuclear polyhedrosis virus with DNA so as to effect recombination thereby producing a mixture of recombinant and non-recombinant baculovirus expression vector for *Autographa californica* nuclear polyhedrosis virus.

This process was facilated by calcium phosphate mediated transfection of the DNA molecules across the cell membrane. The recombination event (allelic transplacement) results in replacement of the AcMNPV polyhedrin gene with the canine parovirus VP-2 gene.

ISOLATION OF THE RECOMBINANT BACULOVIRUS

The recombinant baculovirus was isolated in *Spodoptera frugiperda* tissue culture cells by a focus forming assay. Infection foci arising from CPV 6C2B23. The infections lacked polyhedrin production and produced CPV VP-2 protein.

Isolating the recombinant *Autographa californica* nuclear polyhedrosis virus baculovirus expression vector from said mixture, said expression vector being identified as pAc 6C2B23 and deposited at American Type Culture Collection as designation ATTC 67 682.

PROTECTION OF CANINE

Two SPF Beagle dogs were selected, dog number 1192 and dog number 1193, both of which were seronegative for CPV, one was inoculated with the CPV 6C2B23 infected *Spodoptera fugiperda* tissue culture cells. The inocula of 1 ml was given via the subcutaneous route. The following test data was indicated

| | Hemagglutination (HA)/hemagglutination Inhibition (HI test for CPV) | | | | |
|---|---|---|---|---|---|
| | HI Antibody titer (4 HA Units of CPV-2 Antigen) | | | | |
| Dog # | Pre vac. | 3 wk PV | 4 wk PV2 | 7 wk PV* | 6 dp chall. |
| 1192 (vac) | <10 | 80 | 320 | 320 | 2560 |
| 1193 (control) | — | — | — | <10 | 5120 |

*Challenged with §10⁶ CPV-2′ (virulent virus of "post-1981" type that appears more virulent than our original '78 challenge strain.

Dog response:

1192 (vaccinated):

Normal at all times. Hemagglutinin titers of feces dpi 5–8<1:8. Infection occurred, but not systemic (no verimia). Typical of responses of dogs with other inactivated vaccines.

1193 (control):

Severe illness, with signs (inappetence, fever, lethargy) beginning post-inoculation day 4. Dog vomited, with continuous retching am. of dpc 5: depressed. PM of dpc 5, hemorrhagic diarrhea. Morning of dpi 6 dog was moribund, with bloody diarrhea oozing from anus and blood in vomit. Dog killed (barely alive; rectal temperature 97.3) with overdose of pentabarbitol sodium. At autopsy: small intestine red-purple and lumen filled with bloody material, lymph nodes hemorrhagic, thymus atrophied—e.i., typical signs of sever CPV infection.

Viral HA was only 1:32 in fecal material, but antibody present in high titer in serum and had obviously entered intestine with hemorrhage, neutralizing virus. HA titer of feces at DPI 5 was<1 million.

CONCLUSION.

The baculovirus CPV 6C2B23 recombinant faithfully produced CPV VP-2 protein in insect cells that was immunogenic and protected (1 dog) against challenge with a large dose of highly virulent CPV. As used herein the term permissive host shall include all natural host organisms or derived tissue culture cells as well as any insect or insect tissue culture cells which will support the replication of the baculovirus expression vector and production of VP-2 protein.

While in the foregoing description the detailed embodiments of the present invention have been set forth, it will be understood by those skilled in the art that considerable variation may be made in such detail without departing from the spirit of our invention.

We claim:

1. A prophylactic subunit vaccine for protecting dogs against infection caused by canine parvovirus produced by a recombinant process comprising the steps of:
   a. selecting a Autographa californica nuclear polyhedrisis virus;
   b. using a transfer plasmid known as pAc 6C2B23 for introducing the canine parvovirus VP-2 gene into said *Autograph californica* nuclear polyhedrisis virus by a process known as recombination thereby forming a recombinant virus known as CPV 6C2B23;
   c. inoculating said recombinant virus CPV 6C2B23 into insect tissue culture cells or insects which are permissive hosts for *Autographa californica* nuclear polyhedrisis virus replication and production of VP-2 protein and culturing CPV 6C2B23 in insect tissue culture cells for a time and under conditions sufficient for the production of VP-2 protein; and
   d. recovering the CPV 6C2B23 produced VP-2 protein for inoculation of a canine as a vaccine free of other CPV proteins.

2. A prophylactic subunit vaccine for protecting dogs against infection caused by canine parvovirus produced by a recombinant process comprising:
   a. VP-2 protein free of other CPV proteins produced during replication of CPV 6C2B23 in insect culture cells or insects, which are permissive hosts for *Autographa californica* nuclear polyhedrosis virus replication.

3. A prophylactic vaccine for protecting dogs against infection caused by canine parvovirus comprising VP-2 protein free of other CPV proteins produced during replication of CPV 6C2B23 in *Spodoptera frugiperda* tissue culture cells or *Spodoptera frugiperda* larvae.

4. A prophylactic subunit vaccine for protecting dogs against infection caused by canine parvovirus produced by a recombinant process comprising the steps of:
   a. selecting a baculovirus;
   b. using a transfer plasmid for introducing the canine parvovirus VP-2 gene into said baculovirus by a process known as recombination, thereby forming a recombinant virus CPV baculovirus;
   c. inoculation of recombinant baculovirus into insect tissue culture cells or insects which are a permissive host for the said selected baculovirus replication and production of VP-2 protein free of other CPV proteins and culturing said recombinant baculovirus in insect tissue culture cells for a time and under conditions sufficient for the production of VP-2 protein; and d. recovering the recombinant baculovirus produced VP-2 protein free of other CPV proteins for inoculation into a canine as a vaccine.

5. A prophylactic subunit vaccine for protecting dogs against infection caused by canine parvovirus comprising VP-2 protein free of other CPV proteins produced during replication of a recombinant baculovirus in insect tissue culture cells or insects which are permissive hosts for the replication of selected baculoviruses.

6. A prophylactic subunit vaccine for protecting dogs against infection caused by canine parvovirus comprising VP-2 protein free of other CPV proteins produced during replication of a recombinant baculovirus in a permissive host for replication of the same.

* * * * *